(12) United States Patent
Hunziker

(10) Patent No.: US 7,575,743 B2
(45) Date of Patent: Aug. 18, 2009

(54) COMPOSITIONS AND METHODS FOR THE TREATMENT AND REPAIR OF DEFECTS OR LESIONS IN ARTICULAR CARTILAGE USING SYNOVIAL-DERIVED TISSUE OR CELLS

(75) Inventor: Ernst B. Hunziker, Boll (CH)

(73) Assignee: Orthogene, Inc., Greenbrae, CA (US)

( * ) Notice: Subject to any disclaimer, the term of this patent is extended or adjusted under 35 U.S.C. 154(b) by 20 days.

(21) Appl. No.: 10/060,009

(22) Filed: Jan. 30, 2002

(65) Prior Publication Data

US 2002/0122790 A1 Sep. 5, 2002

Related U.S. Application Data

(60) Provisional application No. 60/265,053, filed on Jan. 30, 2001, provisional application No. 60/265,064, filed on Jan. 30, 2001.

(51) Int. Cl.
*A61K 48/00* (2006.01)
*A61K 9/54* (2006.01)
*A61K 31/70* (2006.01)
*A01N 65/00* (2006.01)
*A01N 43/04* (2006.01)

(52) U.S. Cl. .................. 424/93.21; 424/93.7; 424/458; 514/44

(58) Field of Classification Search .............. 424/93.21, 424/93.2, 423
See application file for complete search history.

(56) References Cited

U.S. PATENT DOCUMENTS

| | | | | |
|---|---|---|---|---|
| 4,378,224 | A | * 3/1983 | Nimni et al. | .................. 8/94.11 |
| 4,506,673 | A | 3/1985 | Bonnell | ...................... 128/419 |
| 4,846,835 | A | 7/1989 | Grande | ......................... 623/11 |
| 5,206,023 | A | 4/1993 | Hunziker | ..................... 424/423 |
| 5,270,300 | A | 12/1993 | Hunziker | ...................... 514/12 |
| 5,368,858 | A | * 11/1994 | Hunziker | ..................... 424/423 |
| 5,486,359 | A | 1/1996 | Caplan et al. | ............... 424/93.7 |
| 5,811,094 | A | 9/1998 | Caplan et al. | ............... 424/93.7 |
| 5,853,746 | A | * 12/1998 | Hunziker | ..................... 424/426 |
| 6,027,743 | A | 2/2000 | Khouri et al. | |
| 6,110,482 | A | * 8/2000 | Khouri et al. | ................ 424/423 |
| 6,254,635 | B1 | * 7/2001 | Schroeder et al. | ........... 623/2.13 |
| 6,413,511 | B1 | * 7/2002 | Glorioso et al. | ............. 44/93.21 |
| 6,530,956 | B1 | * 3/2003 | Mansmann | ............... 623/18.11 |
| 2002/0039567 | A1 | * 4/2002 | Wallimann et al. | .......... 424/85.1 |
| 2002/0098168 | A1 | * 7/2002 | Glorioso et al. | ........... 424/93.21 |

FOREIGN PATENT DOCUMENTS

EP 0267015 B1 9/1992
WO WO 00/48550 8/2000

OTHER PUBLICATIONS

Archer, "Skeletal Development and Osteoarthritis," *Ann. Rheum. Dis.*, 53, pp. 624-630 (1994).
Beaupre et al., "Knee Menisci," *Clin. Orthop. Rel. Res.*, 208, pp. 72-75 (1986).
Buckwalter et al., "Articular Cartilage: Coposition, Structure, Response to Injury, and Methods of Facilitating Repair," *Articular Cartilage and Knee Joint Function: Basic Science and Arthroscopy* (New York: Raven Press, 1990) pp. 19-56.
Buckwalter et al., "Articular Cartilage: Injury and Repair," *Injury and Repair of the Musculoskeletal Soft Tissues* (Park Ridge, Ill.: American Academy of Orthopaedic Surgeons Symposium, 1987) pp. 465-482.
Canalis et al., "Effects of Basic Fibroblast Growth Factor on Bone Formation in Vitro," *J. Clin. Invest.*, 81, pp. 1572-1577 (1988).
Caplan et al., "Principles of Cartilage Repair and Regeneration," *Clin. Orthop.*, 342, pp. 254-269 (1997).
Derynck et al., "Human Transforming Growth Factor-β Complementary DNA Sequence and Expression in Normal and Transformed Cells," *Nature*, 316, pp. 701-705 (1985).
Dickson et al., "Assay of Mitogen-Induced Effects on Cellular Incorporation of Precursors for Scavengers, de novo, and Net DNA Synthesis," *Methods Enzymol.*, 146A, pp. 329-340 (1987).

(Continued)

*Primary Examiner*—Janet L Epps-Smith
(74) *Attorney, Agent, or Firm*—Ropes & Gray LLP

(57) ABSTRACT

Compositions and methods are provided for treatment of cartilage defects in animals and humans. The compositions of the invention include synovial tissue, synovial cells and matrices containing synovial (or cambium) tissue or cells for use in filling a cartilage defect. The matrix and synovial tissue or cell preparations may also contain a proliferation agent, transforming factor or other active agents to promote healing. A controlled-release delivery system may be used to administer the transforming factor. The compositions of the invention also include a synovial covering membrane or devitalized fascial sheet for covering the cartilage defect. The methods of this invention are those in which a minimally invasive surgical intervention is performed to remove a small portion of synovial membrane from a joint. Portions of the synovial membrane, or cells expanded in vitro, are implanted alone or within a matrix, into the defect site, where they produce new cartilage tissue and repair the defect. Alternatively, partially transformed synovial-derived tissue may be formed in situ and implanted into the defect site.

25 Claims, No Drawings

OTHER PUBLICATIONS

Gibble et al., "Fibrin Glue: the Perfect Operative Sealant?," *Transfusion*, 30(8), pp. 741-747 (1990).

Gimenez-Gallego et al., Human Brain-Derived Acidic and Basic Fibroblast Growth Factors: Amino Terminal Sequences and Specific Mitogenic Activities, *Biochem. Biophys. Res. Commun.*, 135(2), pp. 541-548 (1986).

Hunziker et al., Removal of Proteoglycans from the Surface of Defects in Articular Cartilage Transiently Enhances Coverage by Repair Cells, J. Bone Joint Surg., 80(1), pp. 144-150 (1998).

Ichinose et al., "Structure of Transglutaminases," *J. Biol. Chem.*, 265(23), pp. 13411-13414 (1990).

Ingber et al., "Synthetic Analogues of Fumagillin that Inhibit Angiogenesis and Suppress Tumour Growth," *Nature*, 348(6), pp. 555-557 (1990).

Iwamoto et al., "Actions of Hedgehod Proteins on Skeletal Cells," *Crit. Rev. Oral Biol. Med.*, 10(4), pp. 477-486 (1999).

Iwata et al., "Bone Morphogenetic Protein-Induced Muscle- and Synovium-Derived Cartilage Differentiation In Vivo," *Clin. Orthop.*, 296, pp. 295-300 (1993).

Jurgensen et al., "A New Biological Glue for Cartilage-Cartilage Interfaces: Tissue-Transglutaminase," *J. Bone Joint Surg. Am.*, 79(2), pp. 185-193 (1997).

Knutson et al., "Arthrodesis for Failed Knee Arthroplasty," *J. Bone and Joint Surg.*, 67B(1), pp. 47-52 (1985).

Knutson et al., "Arthrodesis After Failed Knee Arthroplasty," *Clin. Orthop.*, 191, pp. 202-211 (1984).

Kolettas et al., "Chondrocyte Phenotype and Cell Survival are Regulated by Culture Conditions and by Specific Cytokines through the Expressino of Sox-9 Transcription Factor," *Rheumatology*, 40, pp. 1146-1156 (2001).

Kuettner, K.E., "Biochemistry of Articular Cartilage in Health and Disease," *Clin. Biochem.*, 25, pp. 155-163 (1992).

Lohmander et al., "Intra-Articular Hyaluronan Injectons in the Treatment of Osteoarthritis of the Knee: a Randomised, Double Blind, Placebo Controlled Multicentre Trial," *Ann. Rheum. Dis.*, 55(7), pp. 424-431 (1996).

Lorand et al, "Transglutaminase," *Mol. Cell. Biochem.*, 58, pp. 9-35 (1984).

Luyten, "Cartilage-Derived Morphogenic Proteins," *Acta Orthop. Scand. Suppl.*, 266, pp. 51-54 (1995).

Majumdar, et al., "BMP-2 and BMP-9 Promote Chondrogenic Differentiation of Human Multipotential Mesenchymal Cells and Overcome the Inhibitory Effect of IL-1," *J. Cell. Physiol.*, 189, pp. 275-284 (2001).

Maquet, "The Biomechanics of the Knee and Surgical Possibilities of Healting Osteoarthritic Knee Joints," *Clin. Orthop.*, 146, pp. 102-110 (1980).

Mitchell et al., "The Deleterious Effects of Drying on Articular Cartilage," *J. Bone Joint Surg.*, 71A(1), pp. 89-95 (1989).

Moses, "A Cartilage-Derived Inhibitor of Neovascularization and Metalloproteinases," *Clinical & Exptl. Rheumatology*, 11(8), pp. 567-569 (1993).

Moses, M.A. et al., "Identification of an Inhibitor of Neovascularization from Cartilage," *Science*, 248, pp. 1408-1410 (1990).

Moses et al., "Isolation and Characterization of an Inhibitor of Neovacularization from Scapular Chondrocytes," J. Cell Bio., 119(2), pp. 475-482 (1992).

Peacock et al., "A Novel Angiogenesis Inhibitor Suppresses Rat Adjuvant Arthritis," *Cellular Immunology*, 160, pp. 178-184 (1995).

Rizzino, "Transforming Growth Factor-β: Multiple Effects on Cell Differentiation and Extracellular Matrices," *Dev. Biol.*, 130(2), pp. 411-422 (1988).

Rizzino, "Soft Agar Growth Assays for Transforming Growth Factors and Mitogenic Peptides," *Methods Enzymol.*, 146A, pp. 341-352 (1987).

Roberts et al., "Purification of Type β Transforming Growth Factors From Nonneoplastic Tissues," *Methods for Preparation of Media, Supplements, and Substrata for Serum-Free Animal Cell Culture*, pp. 181-194 (1984).

Roberts et al., "The Transforming Growth Factor-βs," *Handbook of Experimental Pharmacology*, 95(1), pp. 419-472 (1990).

Rodel et al., "Primary Cultivation of Human Synovial Cells from Nonrheumatic Synovial Tissue and Fluid," *Exp. Toxicol. Pathol.*, 48, pp. 243-247 (1996).

Ruoslathi et al., "Arg-Gly-Asp: A Versatile Cell Recognition Signal," *Cell*, 44, pp. 517-518 (1986).

Seyedin et al., "Cartilage-Inducing Factor-B is a Unique Protein Structurally and Functionally Related to Transforming Growth Factor-β," *J. Biol. Chem.*, 262(5), pp. 1946-1949 (1987).

Seyedin et al., "Cartilage-Inducing Factor-A," *J. Biol. Chem.*, 261(13), pp. 5693-5695 (1986).

Seyedin et al., "Modulation of Chondroblast Phenotype by Transforming Growth Factor-Beta," *Pathol. Immunolpatol. Res.*, 7, pp. 38-42 (1988).

Seyedin et al., "Purification and Characterization of Two Cartilage-Inducing Factors from Bovine Demineralized Bone," *Proc. Natl. Acad. Sci. USA*, 82, pp. 2267-2271 (1985).

St-Jacques et al., "Indian Hedgehog Signaling Regulates Proliferation and Differentiation of Chondrocytes and is Essential for Bone Formation," *Genes Dev.*, 13(16), pp. 2072-2086 (1999).

Steadman et al., "Microfracture: Surgical Technique and Rehabilitation to Treat Chondral Defects," *Clin. Orthop.*, 391S., pp. S362-S369 (2001).

Taguchi et al., "Reconstruction Culture System Simulating Human Synovium: A Three Dimensional Collagen Gel Culture of Synoviocytes," *Cell Struct. Funct.*, 22, pp. 443-453 (1997).

Thomas et al., "Fibroblast Growth Factors: Broad Spectrum Mitogens with Potent Angiogenic Activity," *Trends Biochem. Sci.*, 11, pp. 81-84 (1986).

Webber et al., "Intrinsic Repair Capabilities of Rabbit Meniscal Fibrocartilage: A Cell Culture Model," (30th Ann. Orthop. Res. Soc., Atlanta, Feb. 1984.

Webber et al., "Cell Culture of Rabbit Meniscal Fibrochondrocytes: Proliferative and Synthetic Response to Growth Factors and Ascorbate," *J. Orthop. Res.*, 3, pp. 36-42 (1985).

Weiss, "Joints," Cell and Tissue Biology , 6, pp. 247-253 (1988).

E. B. Hunziker, "Growth-factor-induced healing of partial-thickness defects in adult articular cartilage," *Osteoarthritis and Cartilage*, 9(1):22-32 (2001).

Shirakura K., et al., "Free synovium promotes meniscal-healing; Synovium, muscle and synthetic mesh compared in dogs," Acta Orthopaedica Scandinavica, 68(1):51-54 (1997) abstract.

\* cited by examiner

COMPOSITIONS AND METHODS FOR THE TREATMENT AND REPAIR OF DEFECTS OR LESIONS IN ARTICULAR CARTILAGE USING SYNOVIAL-DERIVED TISSUE OR CELLS

This application claims the benefit under 35 U.S.C. § 119 (e) of U.S. Provisional Application Ser. Nos. 60/265,053 and 60/265,064, both filed on Jan. 30, 2001.

TECHNICAL FIELD OF THE INVENTION

This invention relates to the treatment and repair of defects or lesions (used interchangeably herein) in cartilage. The compositions of the invention include matrices and synovial tissue or cells for use in filling a cartilage defect. Cambium cells may also be used. The matrices and synovial tissue or cell preparations may also contain a proliferation agent and/or transforming factor to facilitate, respectively, expansion of synovial cells and differentiation of synovial cells into chondrocytes, leading to the formation of cartilage tissue. The compositions of the invention also include synovial or cambium cells that have been transfected with chondrogenic genes such that the cells express chondrogenic factors that promote cartilage formation. The methods of the invention comprise obtaining synovial membrane tissue or cells from a minimally invasive biopsy of a joint capsule's synovium, adding appropriate proliferation and/or transforming factors to the synovial membrane tissue or cells and placing the tissue (as a membrane sheet or minced) or cells in the defect with or without a structural matrix. Alternatively, the defect may be filled with layered synovial membrane sheets. The synovial membrane tissue may be partially devitalized prior to filling the defect. Alternatively, the defect may be filled with a matrix containing chondrocytes that have been prepared from synovial cells or cambium cells in vitro or in situ. Alternatively, partially transformed synovial-derived tissue formed in vitro or in situ may be used to fill the defect. The filled defect may then be covered with a covering membrane, preferably comprising a partially devitalized synovial membrane sheet. The methods of this invention are particularly useful in the treatment of articular cartilage defects found in osteoarthritis, and in other diseases and traumas that produce cartilage injury.

U.S. Pat. Nos. 5,206,023, 5,270,300 and 5,853,746 are hereby incorporated by reference.

BACKGROUND ART

Joints are one of the common ways bones in the skeleton are connected. The ends of normal articulated bones are covered by articular cartilage tissue, which permits practically frictionless movement of the bones with respect to one another [L. Weiss, ed., *Cell and Tissue Biology* (Munchen: Urban and Schwarzenburg, 1988) p. 247].

Articular cartilage is characterized by a particular structural organization. It consists of specialized cells (chondrocytes) embedded in an intercellular material (often referred to in the literature as the "cartilage matrix") that is rich in proteoglycans, collagen fibrils of predominantly type II, other proteins, and water [Buckwalter et al., "Articular Cartilage: Injury and Repair," in *Injury and Repair of the Musculoskeletal Soft Tissues* (Park Ridge, Ill.: American Academy of Orthopaedic Surgeons Symposium, 1987) p. 465]. The cartilage matrix is produced and maintained by the chondrocytes embedded within it. Cartilage tissue is neither innervated nor penetrated by the vascular or lymphatic systems. However, in the mature joints of adults, the underlying subchondral bone tissue forms a thin, continuous plate between the bone tissue and the cartilage. This subchondral bone tissue or bone plate is innervated and vascularized. Beneath this bone plate, the bone tissue forms trabeculae, containing the marrow. In immature joints, articular cartilage is underlined by only primary bone trabeculae. A portion of the meniscal tissue in joints also consists of cartilage whose make-up is similar to articular cartilage [Beaupre, A. et al., *Clin. Orthop. Rel. Res.*, pp. 72-76 (1986)].

Two types of defects are recognized in articular surfaces. These are full-thickness defects and superficial defects. Full-thickness defects are those that penetrate into or through the subchondral bone plate; superficial defects are those that do not. These defects differ not only in the extent of physical damage to the cartilage, but also in the nature of the repair response each type of lesion can elicit.

Full-thickness defects of an articular surface include damage to the hyaline cartilage, the calcified cartilage layer and the subchondral bone tissue with its blood vessels and bone marrow. Full-thickness defects can cause severe pain because the bone plate contains sensory nerve endings. Such defects generally arise from severe trauma or during the late stages of degenerative joint disease, such as osteoarthritis. Full-thickness defects may, on occasion, lead to bleeding and the induction of a repair reaction from the subchondral bone [Buckwalter et al., "Articular Cartilage: Composition, Structure, Response to Injury, and Methods of Facilitating Repair," in *Articular Cartilage and Knee Joint Function: Basic Science and Arthroscopy* (New York: Raven Press, 1990) pp. 19-56]. The repair tissue formed is a vascularized, fibrous type of cartilage that has poor biomechanical properties, and that does not persist on a long-term basis [Buckwalter et al. (1990), supra].

Superficial defects in articular cartilage tissue are restricted to the cartilage tissue itself. Such defects are notorious because they generally do not heal and show no propensity for repair reactions.

Superficial defects may appear as fissures, divots, or clefts in the surface of the cartilage, or they may have a "crab-meat" appearance in the affected tissue. They contain no bleeding vessels (blood spots) such as are seen in full-thickness defects. Superficial defects may have no known cause, but often they are the result of mechanical derangements that lead to a wearing down of the cartilaginous tissue. Mechanical derangements may be caused by trauma to the joint, e.g., a displacement of torn meniscus tissue into the joint, meniscectomy, a Taxation of the joint by a torn ligament, malalignment of joints, bone fracture or by hereditary diseases. Superficial defects are also characteristic of early stages of degenerative joint diseases, such as osteoarthritis. Because cartilage tissue is not innervated [*Ham's Histology* (9th ed.) (Philadelphia: J.B. Lippincott Co. 1987), pp. 266-272] or vascularized, superficial defects are typically not painful. However, although painless, superficial defects generally do not heal, and often degenerate into full-thickness defects.

It is generally believed that because articular cartilage lacks a vasculature, damaged cartilage tissue does not receive sufficient or proper stimuli to elicit a repair response [Webber et al., "Intrinsic Repair Capabilities of Rabbit Meniscal Fibrocartilage: A Cell Culture Model", (30th Ann. Orthop. Res. Soc., Atlanta, February 1984); Webber et al., *J. Orthop Res.*, 3 pp. 36-42 (1985)]. It is theorized that chondrocytes in cartilaginous tissue are normally not exposed to sufficient amounts of repair-stimulating agents such as growth factors and fibrin clots typically present in damaged vascularized tissue.

One approach that has been used to expose damaged cartilage tissue to repair stimuli involves drilling or scraping through the cartilage into the subchondral bone to cause bleeding [Buckwalter et al. (1990), supra]. Unfortunately, the repair response of the tissue to such surgical trauma is usually comparable to that observed to take place naturally in full-thickness defects that cause bleeding, viz., formation of a fibrous type of cartilage that exhibits insufficient biomechanical properties and that does not persist on a long-term basis [Buckwalter et al. (1990), supra].

A variety of growth factors have been isolated and are now available for research and biomedical applications [see e.g., Rizzino, A., *Dev. Biol*., 130, pp. 411-422 (1988)]. Some of these growth factors, such as transforming growth factor beta (TGF-β), have been reported to promote formation of cartilage-specific molecules, such as type II collagen and cartilage-specific proteoglycans, in embryonic rat mesenchymal cells in vitro [e.g., Seyedin et al., *Proc. Natl. Acad. Sci. USA*, 82, pp. 2267-71 (1985); Seyedin et al., *J. Biol. Chem*. 261, pp. 5693-95 (1986); Seyedin et al., *J. Biol. Chem.*, 262, pp. 1946-1949 (1987)].

Millions of patients have been diagnosed as having osteoarthritis, i.e., as having degenerating defects or lesions in their articular cartilage. Nevertheless, despite claims of various methods to elicit a repair response in damaged cartilage, none of these treatments has received substantial application [Buckwalter et al. (1990), supra; Knutson et al., *J. Bone and Joint Surg.*, 68-B, p. 795 (1986); Knutson et al., *J. Bone and Joint Surg.*, 67-B, p. 47 (1985); Knutson et al., *Clin. Orthop.*, 191, p. 202 (1984); Marquet, *Clin. Orthop.*, 146, p. 102 (1980)]. And such treatments have generally provided only temporary relief. Systemic use of "chondroprotective agents" has also been purported to arrest the progression of osteoarthritis and to induce relief of pain [Lohmander, L. S. et al., *Ann. Rheum. Dis*., 55(7), pp. 424-31 (1996)]. However, such agents have not been shown to promote repair of lesions or defects in cartilage tissue.

One approach that has been considered is illustrated in U.S. Pat. No. 4,846,835. There, chondrocytes are harvested from mature cartilage tissue that has been removed by biopsy, subsequently grown or expanded in number in tissue culture, and then grafted into the defect site in a collagen gel matrix used to fix the chondrocytes in situ. A periosteal sheet is used to secure the transplanted cells (i.e., the graft) in the defect. This approach suffers from the disadvantages of being more invasive than the instant invention, and creating additional cartilage defects by removing mature cartilage. The use of articular chondrocytes to repair defects is also disadvantaged because articular chondrocytes have a more limited potential for proliferation as compared to synovial cells.

Another approach has been to transform bone marrow-derived mesenchymal stem cells to create chondrocytes in vitro for transplantation into a cartilage defect [Caplan and Haynesworth, U.S. Pat. No. 5,811,094]. These cells can only be obtained through a bone-marrow biopsy, which may be associated with long-term local pathology at the donor site of the patient (usually the iliac crest of the pelvis). Biopsied bone marrow cells then must be purified using sophisticated techniques, expanded in vitro and seeded at the site of the defect [See Caplan et al., *Clin. Orthop.*, 342, pp. 254-269 (1997)].

A further approach found in the literature is applying an electric potential through the tissue surrounding the defect in order to stimulate the growth of new tissue. [U.S. Pat. No. 4,506,673].

Another approach to repairing such defects is found in U.S. Pat. Nos. 5,270,300, 5,206,023, and 5,368,858, in which the present inventor described inventions wherein repair cells are attracted from the synovial compartment to the defect site, where they are induced to proliferate and to differentiate into chondrocytes that synthesize new cartilage matrix.

It has been reported that one means to retain cells in suspension or a matrix within an articular cartilage defect is to suture an appropriate thin covering membrane on the top of the defect space. The covering membrane material used so far has been periosteum-derived, perichondrium-derived or muscle fascia. These covering membranes or other artificial covering membranes have the significant disadvantage that the covering membrane itself does not transform into cartilage tissue, or does so to only a limited extent. Thus the defect space will never fill completely with repair cartilage. Moreover, the degradation of fibrous types of covering membranes is extremely slow. In addition, these covering membranes do not integrate with the native tissue along the defect lesion borders. Such covering membrane tissue may contain fibroblasts, which will not transform into chondrocytes but instead result in undesirable scar-like tissue. Thus, in certain prior art covering membranes, fibroblasts may migrate out into the repair space, contaminate it and lead to unwanted scar tissue formation.

There is, therefore, a need for a simple, fast, and reliable treatment superficial and full-thickness cartilage defects, e.g., as found in cases of severe mechanical injury and osteoarthritis.

SUMMARY OF THE INVENTION

The present invention provides effective therapeutic compositions and methods to induce the repair of lesions in cartilage of humans and other animals. Use of the compositions and methods of this invention also promotes the healing of traumatic lesions and forms of osteoarthritis that would otherwise lead to loss of effective joint function leading to probable resection and replacement of the joint with a metal and/or plastic artificial joint.

In the present invention, the patient suffering from a cartilage defect in a joint is administered a local anesthetic in the joint area, or a general anesthetic may be administered. Appropriate surgical tools are used to extract a portion of synovial membrane tissue. It may be advantageous to take the synovial tissue from the same joint as the defect, as it has been shown that cartilage and synovial cells mature into a form that fulfills the mechanical and structural properties typical of the particular joint from which they are derived. [Kuettner, K. E., *Clin. Biochem.*, 25, pp. 155-63 (1992) (cartilage of different joints differ biochemically); Archer, C. W., *Ann. Rheum. Dis*., 53, pp. 624-30 (1994) (fetal cartilage differs joint to joint)]. In some cases, however, it may be desirable to take synovial tissue from a large joint for use in the repair of a small joint containing an insufficient quantity of donor synovial tissue. The synovial membrane tissue or cells thus procured is used in the repair procedure as described below. Alternatively, the cambium layer from the periosteum or perichondrium can be used as the source of cells or repair tissue.

It is preferred that, prior to filling the defect with the repair materials, the edges of the articular cartilage at the defect site are treated with a proteoglycan-degrading enzyme to remove superficial proteoglycans. This treatment exposes the underlying collagen network, permitting greater tissue integration and adhesion of the repair materials.

In one embodiment of the present invention, synovial membrane tissue is used in an immediate replantation procedure. It is preferred that the synovial membranes or minced synovial membranes are replanted in the presence of a transforming factor that induces differentiation of the synovial cells into chondrocytes that in turn form new cartilage and thereby repair the defect. Preferably, the synovial membranes or minced synovial membranes are distributed in a biodegradable matrix that is then implanted into the defect site. The transforming factor may be administered via a controlled-release delivery system.

In another embodiment of the present invention, minced synovial membranes are subjected to brief collagenase digestion and trypsin digestion (30-45 minutes) followed by a rapid purification in the operating room. These synovial bits are then used for immediate transplantation into the site of the defect, suspended in a biodegradable matrix that includes a transforming factor that will cause them to differentiate into chondrocytes after implantation. Alternatively synovial membrane sheets arranged in stacks can be used to fill the defect. The addition of appropriate transforming factors will promote synovial cell transformation into chondrocytes in situ. Such factors are preferably placed between the synovial membrane sheets. Appropriate anti-angiogenic agents may also be used to prevent vascularization of new cartilage tissue, and appropriate mineralization/calcification inhibitors may be used to prevent ossification of new cartilage tissue.

Alternatively, whole periosteum, perichondrium or, preferably, sheets of the cambium layer of the periosteum or perichondrium are used to fill the defect. Any of several configurations of tissue is possible: bits, sheets, sheets interspersed with bits, tissue suspended in a biodegradable matrix, or combinations of these elements. Also, different tissues may be used in combination. For example, a periosteum cambium layer sheet may be placed on the floor of the defect, a biodegradable matrix containing synovial or periosteal bits may be used to fill the defect and a synovial membrane sheet may be used to cover the defect. Alternatively, mixed layers of synovial membrane sheets and periosteal or perichondrial membrane sheets may be used to fill the defect.

Synovial cells may also be used in an implantation procedure. Synovial cells are obtained from the synovial membrane or fluid, or alternatively, cambium cells are obtained from the cambium layer of the periosteum or perichondrium. If the cells are not of sufficient numbers (as described infra), the cells are then cultured and expanded in vitro. When the cultured cells are expanded to sufficient numbers, they are implanted into the cartilage defect site. Preferably, the cells are implanted in a biodegradable matrix that is implanted into the defect site. The cells are implanted in the presence of a transforming factor that induces differentiation of the synovial cells into chondrocytes that in turn form new cartilage and thereby repair the defect. The transforming factor may be administered via a controlled-release delivery system.

Alternatively, chondrocytes may be isolated from transformed synovial membrane sheets and then implanted into a defect space by inserting them into a matrix or in suspension as described above. Chondrocytes induced this way may also be expanded in vitro before implantation, in order to increase their numbers, and to select for a chondrogenic subpopulation.

In another embodiment of the present invention, synovial cells are induced to differentiate in the presence of a transforming factor in vitro into chondrocytes that begin to form cartilage tissue. Partial enzymatic digestion of the pericellular matrix may be performed to release the individual chondrocytes, which are then implanted in the defect site as a mass. Alternatively, the cartilage tissue formed in vitro may be implanted into a biodegradable matrix that is then in turn implanted into the defect site.

In another embodiment of the present invention, synovial cells may be transformed into chondrocytes in situ. In this aspect of the invention, synovial cells are induced to differentiate in situ through the use of a differentiation-factor-impregnated matrix pad sutured to the synovial membrane in one of the synovial recessi or in proximity to a fat pad. Alternatively, this may be accomplished by attaching the differentiation-factor-impregnated matrix pad to synovial tissue immediately outside of the joint space, eliminating the need to open the joint. The transformed tissue is excised and cells rapidly separated using collagenase and trypsin digestion for about 30-45 minutes. The newly transformed chondrocytes may be further expanded and/or differentiated in vitro before implantation in situ. Chondrocytes may then be implanted at the site of the defect either in suspension (covered by a covering membrane to prevent cell loss into the joint cavity) or in a matrix to retain cells in the defect space. The covering membrane may be sutured to the defect edges near the top perimeter of the lesion.

In each of the foregoing embodiments, it is preferred that the tissue be implanted within a biodegradable matrix to prevent loss of tissue or cells from the defect site, to effectively fill the defect space and as a carrier for any agents or factors employed to treat the defect. Alternatively, or in addition, it is preferred that the surface of the defect site following implanting be covered by a thin biodegradable membrane ("covering membrane") to prevent loss of tissue or cells from the defect site.

In a preferred embodiment of the present invention, a synovial covering membrane, preferably partially devitalized (i.e., partially depleted in macrophages) or fully native, may be used to cover the filled defect. Alternatively, fascial tissue sheets, which may be completely devitalized through three freeze-thaw cycles (to prevent contaminating cell outgrowth following exposure to growth factors in the underlying repair matrix), may be used to cover the defect. Alternatively, the biodegradable membrane may be artificial (e.g., polylactic acid sheets, hyaluronic acid sheets and thin (fine) collagen meshes) or natural (e.g., periosteum, perichondrium). Natural periosteum or perichondrium covering membranes are not preferred when growth factors are used according to this invention, because such factors may stimulate cells in those covering membranes that would contaminate the defect area. However, this is generally not a concern when the cambium layer alone is used.

The use of synovial tissue membranes as a covering membrane to cover an articular cartilage defect has advantages over prior art covering membranes comprising periosteal tissue or fascia. Synovial tissue can be more completely transformed into chondrocytes and cartilage and better integrated into adjacent cartilage tissue. Both periosteal tissue and fascia typically contain many fibroblasts, which cannot be transformed into chondrocytes and cartilage, and which persist as scar tissue. Synovial tissue membranes, without additional therapeutic agents in the defects beneath them, through transformation into chondrocytes and cartilage can be adequate to repair shallow defects.

When using synovial tissue as a covering membrane, it is preferred that the tissue be treated with a transforming factor. It is also preferable that the transforming factor is used in association with a controlled-release delivery system. The transforming factor, with or without the controlled-release delivery system, can be added to the synovial covering membrane, or the synovial covering membrane can be soaked in a solution of transforming factor, with or without a controlled-release delivery system.

The present invention is a simpler and more rapid procedure than those in the prior art. For example, the present invention does not require the presence of attractive factors to induce migration of repair cells into the defect site, and it does not require the complicated extraction and purification procedures necessary to utilize bone marrow-derived mesenchymal cells.

In the knee, synovial tissue can be excised from recessi near the retropatellar fat pad or in the suprapatellar recessus where large reserve folds of synovial tissue are present. Such removal of synovial tissue involves virtually no impairment of joint function. Removal of pads of synovial membrane is not associated with any joint pathology, and any lesions in these tissues tend to heal spontaneously.

The use of the synovial tissue covering membrane of the present invention to cover the filled defect also has a significant advantage over the methods of the prior art in that the whole covering membrane itself is capable of transforming into cartilage tissue and integrating into the newly forming repair cartilage. Moreover, it can integrate well with the adjoining native tissue, such as bone. In addition, it is advantageous when transforming growth factors are used because the synovial tissue covering membrane contains primarily chondrogenic precursor cells.

The use of partially devitalized tissue covering membranes according to the present invention is also advantageous. Alternatively, a fascial covering membrane may be used. Preferably, such a fascial covering membrane will be fully devitalized prior to use (i.e., frozen and thawed three times prior to use) in order to prevent fibroblasts, macrophages and other cell types from contaminating the newly formed cartilage tissue and subsequently forming undesirable scar tissue.

For synovial tissue covering membranes, partial devitalization is preferred for selectively removing macrophages, but not other cell types. This is accomplished through a single freeze-thaw cycle, or other means known in the art for the selective removal of macrophages and other inflammatory cells (e.g., macrophages may be removed from synovial or other tissue by using anti-macrophage antibodies or other substances to selectively neutralize macrophages).

In each of the above embodiments, anti-inflammatory agents may be used locally to prevent macrophage migration, activation and proliferation, as well as pannus formation. Anti-inflammatory agents include steroidal drugs such as prednisone, and non-steroidal anti-inflammatory drugs ("NSAIDs") such as ibuprofen, ketoprofen, piroxicam, naproxen, sulindac, aspirin, choline subsalicylate, diflunisal, fenoprofen, indomethacin, meclofenamate, salsalate, tolnetin and magnesium salicylate. Such anti-inflammatory agents may be administered to the defect in a controlled-release delivery system in a matrix containing synovial tissue or cells, or placed between layered synovial membrane sheets. Examples of delivery systems include poly(lactic) acid (PLA), poly(D,L-lactic-co-glycolic) acid (PLGA) or poly (epsilon-caprolactone) (PCL) microspheres, liposomes, bioerodible polymers, collagen fibers chemically linked to heparin sulfate proteoglycans, and carbohydrate-based corpuscles.

In each of the above embodiments, cartilage repair may be carried out through autologous transplantation of synovial tissue or cells, i.e., from the same individual, or alternatively, heterologous transplantation of synovial tissue or cells may be carried out. Heterologous transplantation may require simultaneous administration of immunosuppressant therapies known in the art.

The synovial tissue covering membranes of the present invention may also be used with other cartilage repair techniques known in the art, including but not limited to those described in U.S. Pat. Nos. 5,206,023, 5,270,300 and 5,853, 746.

DETAILED DESCRIPTION OF INVENTION

In order that the invention may be more fully understood, the following detailed description is provided. In the description the following terms are used.

Anti-Angiogenic Agent—as used herein, refers to any compound or composition with biological activity that prevents ingrowth of blood vessels from the underlying bone tissue into the cartilage tissue, such as anti-invasive factors, cartilage-derived angiogenesis inhibitors, angiostatin, metalloprotease inhibitors, antibodies against angiogenesis-inducing factors (including bFGF and endothelial cell stimulating angiogenic factor (ESAF)), Suramin (Germanin®, Bayer AG, Germany), fumagillin, fumagillin analogues and AGM-1470 [Peacock, D. J. et al., *Cellular Immunology*, 160, pp. 178-84 (1995)]. In vivo and in vitro assays to determine anti-angiogenic agents are well-known in the art [e.g., Moses, M. A., *Clinical & Exptl. Rheumatology*, 11 (Suppl. 8), pp. 567-69 (1993); Moses, M. A. et al., *J. Cell Bio.*, 119(2), pp. 475-82 (1992); Moses, M. A. et al., *Science*, 248, pp. 1408-10 (1990); Ingber, D. et al., *Nature*, 348(6), pp. 555-57 (1990)].

Arthroscopy—as used herein, refers to the use of an arthroscope to examine or perform surgery on a joint.

Cambium Cells—as used herein, refers to cells found in the cambium layer of the perichondrium and periosteum of joints and bones.

Cartilage—as used herein, refers to a type of connective tissue that contains chondrocytes embedded in an intercellular material (often referred to as the "cartilage matrix") comprising fibrils of collagen (predominantly type II collagen along with other minor types, e.g., types IX and XI), various proteoglycans (e.g., chondroitinsulfate-, keratansulfate-, and dermatansulfate proteoglycans), other proteins, and water. Cartilage as used herein includes articular and meniscal cartilage. Articular cartilage covers the surfaces of the portions of bones in joints and allows movement in joints without direct bone-to-bone contact, and thereby prevents wearing down and damage to apposing bone surfaces. Most normal healthy articular cartilage is also described as "hyaline," i.e., having a characteristic frosted glass appearance. Meniscal cartilage is usually found in joints that are exposed to concussion as well as movement. Such locations of meniscal cartilage include the temporo-mandibular, sterno-clavicular, acromio-clavicular, wrist and knee joints [*Gray's Anatomy* (New York: Bounty Books, 1977)].

Cell Adhesion Promoting Factor—as used herein, refers to any compound or composition, including fibronectin and other peptides as small as tetrapeptides, that comprises the tripeptide Arg-Gly-Asp, which mediates the adhesion of cells to extracellular material [Ruoslathi et al., *Cell*, 44, pp. 517-518 (1986)].

Chondrocytes—as used herein, refers to cells that are capable of producing components of cartilage tissue, e.g., type II cartilaginous fibrils and fibers and proteoglycans.

Covering membrane—as used herein, refers to any material that can be used to cover a filled defect site following implantation to prevent loss of cells into the adjoining space, as well as any material that can be placed between the bone defect portion and the cartilage defect portion of a full thickness defect and that prevents cell migration and blood vessel infiltration from the bone defect portion into the cartilage defect portion of the full thickness defect. The membranes used in the methods and compositions of this invention are preferably biodegradable, and may include synovial membranes, polylactic acid sheets, hyaluronic acid sheets, thin (fine) collagen meshes, periosteum, perichondrium or fascia. Synovial membranes typically are transformed into cartilage tissue, becoming integrated into the repair cartilage tissue. Non-biodegradable membranes may include teflon (Goretex®), Millipore® membrane, or Verigen®membrane.

Fibroblast growth factor (FGF)—any member of the family of FGF polypeptides [Gimenez-Gallego et al., *Biochem. Biophys. Res. Commun.*, 135, pp. 541-548 (1986); Thomas et al., *Trends Biochem. Sci.*, 11, pp. 81-84 (1986)] or derivatives thereof, obtained from natural, synthetic or recombinant sources, which exhibits the ability to stimulate DNA synthesis and cell division in vitro [for assays see, e.g., Gimenez-Gallego et al., 1986, supra; Canalis et al., *J. Clin. Invest.*, 81, pp. 1572-1577 (1988)] of a variety of cells, including primary fibroblasts, chondrocytes, vascular and corneal endothelial cells, osteoblasts, myoblasts, smooth muscle and glial cells [Thomas et al., 1986, supra]. FGF's maybe classified as acidic (aFGF) or basic (bFGF) FGF, depending on their isoelectric points (pI).

Matrix—as used herein, refers to a porous composite, solid or semi-solid substance having pores or spaces sufficiently large to allow cells to populate the substance. The term matrix includes matrix-forming materials, i.e., materials that can form matrices within a defect site in cartilage or bone. Matrix-forming materials may require addition of a polymerizing agent to form a matrix, such as adding thrombin to a solution containing fibrinogen to form a fibrin matrix. Other matrix materials include but are not limited to collagen, combinations of collagen and fibrin, agarose (e.g., Sepharose®), gelatin, hyaluronic acid (hyaluronan), hyaluronic acid in combination with collagen, photo-polymerizable matrices, albumin-based matrices, polylactic acid-based matrices, polyglycolic acid-based matrices and fibrin-based matrices. Calcium phosphates, such as tricalcium phosphate, hydroxyapatite or other calcium salts that form solid matrices may be used alone or in combination with other matrix materials in treating defects in bones.

Proliferation (mitogenic) Agent—as used herein, refers to any compound or composition, including peptides, proteins, and glycoproteins, that is capable of stimulating proliferation of cells in vitro. In vitro assays to determine the proliferation (mitogenic) activity of peptides, polypeptides and other compounds are well-known in the art [see, e.g., Canalis et al., 1988, supra; Gimenez-Gallego et al., *Biochem. Biophys. Res. Commun.*, 135, pp. 541-548 (1986); Rizzino, "Soft Agar Growth Assays for Transforming Growth Factors and Mitogenic Peptides", in *Methods Enzymol.*, 146A (New York: Academic Press, 1987), pp. 341-52; Dickson et al., "Assay of Mitogen-Induced Effects on Cellular Incorporation of Precursors for Scavengers, de novo, and Net DNA Synthesis", in *Methods Enzymol.*, 146A (New York: Academic Press, 1987), pp. 329-40]. One standard method to determine the proliferation (mitogenic) activity of a compound or composition is to assay it in vitro for its ability to induce anchorage-independent growth of nontransformed cells in soft agar [e.g., Rizzino, 1987, supra]. Other mitogenic activity assay systems are also known [e.g., Gimenez-Gallego et al., 1986, supra; Canalis et al., 1988, supra; Dickson et al., 1987, supra]. Mitogenic effects of agents are frequently very concentration-dependent, and their effects may be reversed at lower or higher concentrations than the optimal concentration range for mitogenic effectiveness.

Synovial Cell—as used herein, refers to a cell physiologically associated with the synovial membrane or present in the subsynovial space; a cell obtained from a joint's synovial membrane or synovial fluid. When exposed to appropriate stimuli, the synovial cell will differentiate and be transformed into a chondrocyte. Synovial-derived repair cells include mesenchymal cells, fibroblasts, fibroblast-like cells, macrophages, de-differentiated chondrocytes, synovial lining cells, and synovial fibroblast-like cells.

Transforming Factor—as used herein, refers to any peptide, polypeptide, protein, or any other compound or composition that induces differentiation of, e.g., synovial-derived cells into chondrocytes. This also includes the products of genes introduced (e.g., by transfection) into cells used to repair the defect. The ability of the compound or composition to induce or stimulate production of cartilage-specific proteoglycans and type II collagen by cells can be determined by in vitro assays known in the art [Seyedin et al., *Proc. Natl. Acad. Sci. USA*, 82, pp. 2267-71 (1985); Seyedin et al., *Path. Immunol. Res.*, 7, pp. 38-42 (1987)].

Transforming Growth Factor Beta (TGF-β)—any member of the family of TGF-β polypeptides [Derynck, R. et al., *Nature*, 316, pp. 701-705 (1985); Roberts et al., "The transforming growth factor-β's", In *Peptide growth factors and their receptors I* (Berlin: Springer Verlag, 1990), p. 419)] or derivatives thereof, obtained from natural, synthetic or recombinant sources, that exhibits the characteristic TGF-β ability to stimulate normal rat kidney (NRK) cells to grow and form colonies in a soft agar assay [Roberts et al., "Purification of Type β Transforming Growth Factors From Non-neoplastic Tissues", in *Methods for Preparation of Media, Supplements, and Substrata for Serum-Free Animal Cell Culture* (New York: Alan R. Liss, Inc., 1984)] and that is capable of inducing transformation of synovial-derived repair cells into chondrocytes as evidenced by the ability to induce or stimulate production of cartilage-specific proteoglycans and type II collagen by cells in vitro [Seyedin et al., 1985, supra].

Preparing the Defect and Obtaining Synovial Tissue

To carry out the methods of treating defects or lesions in cartilage according to this invention, an articular cartilage defect to be repaired is first identified. Cartilage defects in animals are readily identifiable visually during arthroscopic examination of the joint or during simple examination of the lesion or defect during open surgery. Cartilage defects may also be identified inferentially by using computer aided tomography (CAT scanning), X-ray examination, magnetic resonance imaging (MRI), analysis of synovial fluid or serum markers, or by any other procedure known in the art.

Once a defect has been identified, prior to, or at the time of repair, the surgeon may elect to surgically modify the defect to enhance the ability of the defect to physically retain the synovial membrane tissue, cells and/or matrix material that is added in the treatment methods described herein. Preferably, instead of having a flat or shallow concave geometry, the defect has, or is shaped to have, vertical edges or is undercut in order to better retain the synovial membrane tissue, cells and/or matrix materials added in the treatment methods described herein. Both full-thickness and shallow defects may be treated to create discrete areas of bleeding in a process called "microfracture," which involves making measured perforations in the subchondral bone plate. Released marrow elements form a surgically induced clot that provides an enriched environment for new tissue formation [Steadman et al. *Clin. Orthop.*, 391*Suppl.*, pp. S362-69 (October 2001)].

In one embodiment, under local anesthesia, a small arthroscopic or surgical intervention is performed. The defect site may optionally be treated prior to implantation with a proteoglycan-degrading enzyme or other materials to improve adhesion of the replanted synovial membrane tissue, cells or matrix. The surface of the defect is dried by blotting the area using sterile absorbent tissue, and the defect volume is filled with a sterile enzyme solution for a period of 2-10 minutes to degrade the proteoglycans present on the surface of the cartilage and locally within approximately 1 to 2 µm deep from the surface of the defect. Various enzymes may be used, singly or in combination, in sterile buffered aqueous solutions to degrade the proteoglycans. The pH of the solution should be adjusted to optimize enzyme activity.

Enzymes useful to degrade the proteoglycans in the methods of this invention include chondroitinase ABC, chondroitinase AC, hyaluronidase, pepsin, trypsin, chymotrypsin, papain, pronase, stromelysin and Staph V8 protease [Jurgensen, K. et al., *J. Bone Joint Surg. Am.*, 79(2), pp. 185-93 (1997); Hunziker, E. B. et al., *J. Bone Joint Surg. Br.*, 80(1), pp. 144-50 (1998)]. The appropriate concentration of a particular enzyme or combination of enzymes will depend on the activity of the enzyme solution.

In a preferred embodiment of this invention, the defect is filled with a sterile solution of chondroitinase AC at a concentration of 1 U/ml and digestion is allowed to proceed for 4 minutes. The preferred concentration of chondroitinase AC is determined according to the procedure described in Example 1. Any other enzyme used should be employed at a concentration and for a time period such that only superficial proteoglycans down to a depth of about 1-2 µm are degraded.

The amount of time the enzyme solution is applied should be kept to a minimum to effect the degradation of the proteoglycans predominantly in the repair area. For chondroitinase ABC or AC at a concentration of 1 U/ml, a digestion period longer than 10 minutes may result in the unnecessary and potentially harmful degradation of the proteoglycans outside the defect area. Furthermore, digestion times longer than 10 minutes contribute excessively to the overall time of the procedure. The overall time for the procedure should be kept to a minimum especially during open arthrotomy, because cartilage may be damaged by exposure to air [Mitchell et al., (1989), supra]. For these reasons, in the embodiments of the methods of this invention that include the step of degradation of proteoglycans by enzymatic digestion, digestion times of less than 10 minutes are preferred and digestion times of less than 5 minutes are most preferred.

According to the methods of this invention, after the enzyme has degraded the proteoglycans from the surface of the defect, the enzyme solution should be removed from the defect area. Removal of the enzyme solution may be effected by using an aspirator equipped with a fine suction tip followed by sponging with cottonoid. Alternatively, the enzyme solution may be removed by sponging up with cottonoid alone.

Following removal of the enzyme solution, the defect should be rinsed thoroughly, preferably three times, with sterile physiologic saline (e.g., 0.15 M NaCl). The rinsed defect site should then be dried. Sterile gauze or cottonoid may be used to dry the defect site.

For intraoperative synovial membrane replantation or implantation, proteoglycan degrading enzymes must be washed out extensively in order to remove any proteases and thus prevent the inactivation of added growth factors.

Alternatively, or in addition to the enzyme treatment step, the defect site may be dressed with a compound, such as fibrin glue or transglutaminase, to enhance adhesion of the matrix to the defect site. In a preferred embodiment, fibrin glue or transglutaminase is applied to the defect site after the defect site has been rinsed and dried following enzyme treatment. Fibrin glue promotes chemical bonding (cross-linking) of the fibrils of the matrix to the cartilage collagen fibrils on the defect surface [see Gibble et al., *Transfusion*, 30(8), pp. 741-47 (1990)]. The enzyme transglutaminase may be used to the same effect [see e.g., Ichinose et al., *J. Biol. Chem.*, 265(23), pp. 13411-14 (1990); "Transglutaminase," Eds: V. A. Najjar and L. Lorand, Martinus Nijhoff Publishers (Boston, 1984)]. Suturing, cauterization or compounds other than fibrin glue or transglutaminase that can promote adhesion of extracellular materials may also be used.

A patient suffering from the defect is anesthetized locally in the joint containing the defect or given a general anesthetic, and appropriate surgical tools (e.g., a biopsy set, scalpel or arthroscope) are used to extract an appropriate amount of synovial membrane and/or synovial fluid from the joint. In the knee joint, synovial membrane material is preferably removed from the distal recessus near or from the fat pad in the knee joint or in the suprapatellar recessus. Synovial membrane tissue including fat pad tissue may also be used when additional tissue bulk is useful to completely fill the defect. Generally, synovial membrane should be removed from areas lying in reserve folds and not directly opposing articular cartilage surfaces.

Use of Synovial Membrane Tissue

Synovial membrane tissue obtained may be used in a rapid intraoperative synovial membrane implantation procedure. Synovial membrane tissue may optionally be partially devitalized with a single freeze-thaw cycle and then placed within the defect. A matrix containing a proliferation agent and/or transforming factor may optionally be used together with the synovial membrane tissue to fill the defect.

In one embodiment of the present invention, synovial membrane tissue is directly implanted into the defect site. In order to prevent loss of the implanted synovial membrane tissue into the joint space, the surface of the defect site may be covered with a thin biodegradable covering membrane. This covering membrane may be artificial or natural (e.g., synovial membrane, as described below). The covering membrane is sealed to the edges of the defect site with sutures, fibrin glue, tissue transglutaminase, cauterization or the like. If sutures are used in conjunction with a synovial membrane, the sutures may be impregnated with a transforming factor such as BMP-2 at an appropriate concentration to promote differentiation of the synovial cells in the membrane into chondrocytes.

In another embodiment of the present invention, synovial membranes are removed from recessi and cut up into very small pieces (i.e., minced into small bits) for transplantation. Minced synovial membranes may be subjected to brief collagenase digestion and trypsin digestion (30-45 minutes) followed by a rapid purification in the operating room. Alternatively, cambium tissue may be obtained and minced by physical scraping and/or gentle proteolytic digestion of periosteum or perichondrium tissue. The minced synovial membranes or cambium tissue are mixed into a matrix and transplanted within the matrix into the defect space. It is preferred that the matrix contains a chemotactic/proliferation agent in order to populate the whole matrix with cells and a transforming factor with a controlled-release system in order to induce cartilage tissue transformation within this matrix. The whole matrix may be covered with a synovial tissue covering membrane or other membrane to retain the matrix within the defect space.

In another embodiment of the present invention, one or more layers of excised synovial membrane sheets are stacked one on top of the other until the defect space is filled. The edges of the top layer and, optionally, the corners of the lower layers, may be sutured or glued to the defect edges to retain the whole stack in situ. Between the sheets, transforming growth factors are deposited in order to induce cartilage transformation of the synovial membrane sheets, preferably using a controlled-release delivery system as described above. This may be done by depositing, between the sheets, a thin matrix layer (e.g., fibrin or collagen) impregnated with a transforming factor to induce the tissue to transform into cartilage. Alternatively, transforming factors contained in microsomes, microspheres, nanospheres or liposomes could be added between the synovial membrane sheets without a matrix. Another embodiment is to place an emulsion containing such factors between the sheets. Alternatively, the synovial membrane sheets may be soaked in a transforming growth factor-containing solution before replantation.

The minced synovial membrane, minced cambium tissue and synovial membrane sheets of the above embodiments may also be partially devitalized through a single freeze-thaw cycle in order to reduce cell density and reduce the presence of unwanted cells. Alternatively, anti-macrophage antibodies or other substances may be used to deplete the macrophage population.

Partially transformed synovial membrane tissue may also be used to fill a defect space. In a first surgical intervention, matrix pads, impregnated with transforming growth factors for slow release, are sutured and attached to recessi of synovial membrane in a joint, or alternatively attached to synovial tissue immediately outside the synovial capsule. Eight to fourteen days after this intervention, the tissue beneath such a matrix pad will have been transformed into cartilage-like tissue. This is then removed and stacked one on top of another in the defect site to fill the defect space with the partially transformed synovial tissues. Additional transforming factors as well as maintenance factors known in the art (e.g., IGF I, IGF II and IGF-BP's) may be added between the layers of such tissue stacks.

In areas where defects extend to vascularized tissues such as subchondral bone and subchondral bone marrow spaces (or near synovial membranes that are heavily vascularized), there is a possibility that ingrowing blood vessels may contaminate the repair tissue in the defect. In order to prevent such undesirable vascular ingrowth, anti-angiogenic factors may be added to the matrix or deposited between the synovial tissue layers, among the synovial bits or among the synovial-derived transplanted chondrocytes or synovial cells.

Use of Synovial Cells

The synovial membrane sample obtained as described above is partially digested such that the individual synovial lining cells and subsynovial fibroblast-like cells are released from the membranous tissue. Standard trypsinization may be used or other means of dissociating the cells from the surrounding tissue. The individual cells are collected (e.g., via differential sedimentation through a ficoll density gradient) and cultured in vitro under standard cell culture conditions ensuring their rapid proliferation and expansion (a proliferation agent may be added to more rapidly effect this step). Synovial cell culturing techniques are known in the art [Taguchi, K. et al., *Cell Struct. Funct.*, 22, pp. 443-53 (1997), Rodel, J. et al., *Exp. Toxicol. Pathol.*, 48, pp. 243-7 (1996)]. Within a few weeks, the synovial cells will have expanded to sufficient numbers (e.g., 10,000 to 300,000 cells per milliliter of solution or matrix), depending on the size of the defect, to be ready for implantation into the defect site.

In another embodiment of the present invention, cultured synovial cells are induced to differentiate in vitro. It has been shown that mesenchymal stem cells can be induced to differentiate in vitro [Caplan and Haynesworth, U.S. Pat. No. 5,486,359]. It has also been shown that synovium-derived mesenchymal-type cells stimulated in vitro with BMP (bone morphogenetic protein) differentiate into cartilage [Iwata et al., *Clin. Orthop.*, 296, pp. 295-300 (1993)].

In this embodiment, synovial cells removed from a patient are cultured in the presence of TGF-β and/or BMP (preferred concentrations are provided below) in order to induce differentiation into chondrocytes. The resulting chondrocytes are then implanted into the defect site as in the previously described embodiments, that is, either as a suspension or as part of a matrix system.

In an additional embodiment, synovial cells induced to differentiate into chondrocytes by TGF-β and/or BMP are allowed to produce cartilage tissue in vitro. Cartilage tissue thus produced is implanted into the defect site after molding the size and shape of the cartilage tissue to snugly fit the defect. Alternatively, the cartilage matrix may be subjected to partial enzymatic digestion in order to collect cartilage-producing chondrocytes, which are then implanted as a suspension or mass.

Use of Synovial Tissue Covering Membranes

When using synovial membranes as covering membranes, it is preferred that a partial devitalization step be carried out because this tissue contains macrophages, which are not ideal for cartilage tissue formation, as they may lead to the proliferation of inflammatory cells or produce signal substances that may attract blood vessels and thus lead to unwanted ossification. Macrophages may be removed by a single quick-freeze and thaw process that reduces the number of cells in the synovial covering membrane. This primarily removes macrophages, while mesenchymal cell numbers, although decreased, remain adequate for chondrocyte formation and thus eventual cartilage formation. In addition, the partial devitalization, by reducing the cell density, will create a more appropriate physiological cell density for cartilage formation in the repair tissue. Other methods known in the art for removing macrophages (e.g., anti-macrophage antibodies) may be employed in addition or as an alternative.

Instead of the immediate synovial tissue autotransplantation step for covering a defect as described above, a pre-transformed synovial membrane may be used. In this approach, a two-step surgical method is employed. The first step is an arthroscopic intervention wherein a matrix pad that is impregnated with a transforming factor (e.g., BMP-2, TGF-β) is sutured (1) to the synovial membrane in a recessus, (2) to synovial tissue immediately outside the synovial space, including the fat pad or (3) to subsynovial connective tissue, close to the synovial lining cells. Options (2) and (3) have the advantage that the joint does not need to be opened. Three to four weeks later, apposing this matrix pad, the synovial membrane will have become transformed into cartilage-like tissue. The second step is a surgical intervention wherein this cartilage-like tissue area is excised and transplanted into the defect site in order to fill and/or cover the defect. In a small joint with a very thin articular cartilage layer (e.g., a finger joint) such a partially transformed synovial membrane may suffice to fill the whole defect space. Such a partially transformed synovial membrane induced in the knee joint and autotransplanted into a small finger joint (or other joint) may be useful for reconstruction purposes.

Synovial covering membranes used according to the present invention as a cover to retain tissue and/or matrix material may be oriented upside down or in the physiological direction; each way will be operative. It may be applied as fully vital or partially devitalized material in order to eliminate specific cell types to optimize the outcome.

In one embodiment involving the use of synovial covering membranes according to the instant invention, a synovial covering membrane may be used to cover the floor of a full-thickness defect, or the bottom surface of a microfractured full-thickness or shallow defect (that just reaches the subchondral bone plate). Such a covering membrane may function as a structural and functional barrier in these defects. In full thickness or shallow defects containing one or more bleeding points, an osteogenic factor, optionally with a controlled-release system (e.g., microspheres, liposomes or contained in a matrix), may be placed at the base of the bone portion of the defect, and then covered with a first synovial covering membrane. Optionally, an angiogenic agent may be placed under the first synovial covering membrane to further promote bone formation, although factors in the blood will also promote bone formation. The first synovial covering membrane may be held in place using sutures, cauterization, glue, other means, or nothing at all. An anti-angiogenic agent may be used at the perimeter of the first synovial covering membrane to inhibit invasion of the cartilage repair space above by blood vessels.

Above the first synovial covering membrane, i.e., not adjacent to the bone portion of the defect, chondrogenic agents may be used with or without a matrix to promote cartilage formation. It is preferred that stacks of synovial membranes are used to fill the defect, interleaved with chondrogenic agent. Cell-based therapies may also be used instead of synovial membrane stacks, with or without a matrix, to promote cartilage formation. Such cell-based therapies include the use of synovial cells, chondrocytes, bone marrow stromal cells, cells transfected with chondrogenic genes or any chondrogenic cell/matrix system.

The top of the defect void, after having been filled with chondrogenic cell/matrix system, is preferably covered by a second synovial covering membrane that may directly overlay chondrogenic agents in order to promote its complete transformation into cartilage tissue and to simultaneously function as a retention device for the chondrogenic cell/matrix system filling the defect void.

The first synovial covering membrane according to the above embodiment may function as an anchoring device, performing three repair functions in the full-thickness defect: (1) the side of the synovial covering membrane facing the bone portion of a full-thickness defect, or the bleeding points of a shallow defect, will participate in the formation of bone and will eventually fuse with newly formed bone over a period of approximately one to four weeks; (2) the side of the synovial covering membrane facing away from the bone portion of the defect will participate in the formation of cartilage and will eventually fuse with newly formed cartilage; and (3) the first synovial covering membrane itself will function as a transient barrier to blood vessel upgrowth from the bone portion or from the fat tissue of the defect and also as a barrier to unwanted migration and contamination by stem cells of various origins from bone and fat tissue into the cartilage repair space of the defect.

Matrices and Other Repair Materials

Matrix materials useful in the methods of this invention for filling or otherwise dressing cartilage defects include fibrinogen (activated with thrombin to form fibrin in the defect or lesion), collagen, agarose, gelatin and any other biodegradable material that forms a matrix with pores sufficiently large to allow synovial cells or chondrocytes to populate and proliferate within the matrix and that can be degraded and replaced with cartilage during the repair process.

The matrices useful in the methods of this invention may be preformed or may be formed in situ, for example, by polymerizing compounds and compositions such as fibrinogen to form a fibrin matrix. Matrices that may be preformed include collagen (e.g., collagen sponges and collagen fleece), chemically modified collagen, gelatin beads or sponges, a gel-forming substance such as agarose, and any other gel-forming or composite substance that is composed of a matrix material that will fill the defect and allow cultured or native synovial cells or chondrocytes to populate the matrix, or mixtures of the above.

In one embodiment of this invention, the matrix is formed using a solution of fibrinogen and minced synovial tissue, to which is added thrombin to initiate polymerization shortly before use. A fibrinogen concentration of 0.5-5 mg/ml of an aqueous buffer solution may be used. Preferably, a fibrinogen solution of 1 mg/ml of an aqueous buffer solution is used. Polymerization of this fibrinogen solution in the defect area yields a matrix with a pore size sufficiently large (e.g., approximately 50-200 µM) so that synovial cells or chondrocytes are free to populate the matrix and proliferate in order to fill the volume of the defect that the matrix occupies. Preferably, a sufficient amount of thrombin is added to the fibrinogen solution shortly before application in order to allow enough time for the surgeon to deposit the material in the defect area prior to completion of polymerization. Typically, the thrombin concentration should be such that polymerization is achieved within a few to several (2-4) minutes since exposure of cartilage to air for lengthy periods of time has been shown to cause damage [Mitchell et al., *J. Bone Joint Surg.*, 71*A*, pp. 89-95 (1989)]. Excessive amounts of thrombin should not be used since thrombin has the ability to cleave growth factor molecules and inactivate them. Thrombin solutions of 10-500 units per ml, and preferably 100 units per ml, of an aqueous buffer solution may be prepared for addition to the fibrinogen solution.

In a preferred embodiment of this invention, approximately 20 µl of thrombin (100 U/ml) are mixed with each ml of a fibrinogen solution (1 mg/ml) approximately 200 seconds before filling the defect. Polymerization will occur more slowly if a lower concentration of thrombin is added. It will be appreciated that the amount of thrombin solution needed to achieve fibrin polymerization within 2-4 minutes can be given only approximately, since it depends upon the environmental temperature, the temperature of the thrombin solution, the temperature of the fibrinogen solution, etc. Alternatively, where convenient, the thrombin may be added by placing it on top of the matrix solution after the solution has been placed in the defect site and allowing it to diffuse through the solution. The polymerization of the thrombin-activated matrix solution filling the defect is easily monitored by observing the thrombin-induced polymerization of an external sample of the fibrinogen solution. Preferably, in the compositions and methods of this invention, fibrin matrices are formed from fibrinogen molecules derived from the blood of the same mammalian species as the species to be treated. Non-immunogenic fibrinogen from other species may also be used.

Matrices comprising fibrin and collagen or, more preferably, fibrin and gelatin may also be used in the compositions and methods of this invention. Collagenous matrices may also be used in repairing cartilage defects, including full thickness defects. Note that for repairing the bone portion of deep full-thickness defects, the procedures disclosed in U.S. Pat. Nos. 5,270,300 and 5,853,746 may be employed.

When collagen is used as a matrix material, sufficiently viscous solutions can be made, e.g., using Collagen-Vliess® ("fleece"), Spongostan®, or gelatine-blood-mixtures, and there is no need for a polymerizing agent. Collagen matrices may also be used with a fibrinogen solution activated with a polymerizing agent so that a combined matrix results.

Polymerizing agents may also be unnecessary when other biodegradable compounds are used to form the matrix. For example, Sepharose® solutions may be chosen that will be liquid matrix solutions at 39-42° C. and become solid (i.e., gel-like) at 35-38° C. The Sepharose should also be at concentrations such that the gel filling the defect has a mesh size to allow the synovial-derived repair cells or chondrocytes to freely populate the matrix and defect area.

Use of Transforming Factors and Matrices

The replanted synovial membrane tissue or synovial cell suspension, once in the defect site, may partially spontaneously transform into chondrocytes that ultimately produce mature cartilage tissue, initially adhering to the surfaces treated with the proteoglycans-degrading enzyme [Hunziker, E. B. et al., *J. Bone Joint Surg. Br.*, 80(1), pp. 144-50 (1998)]. Preferably, a suitable concentration of a transforming factor such as transforming growth factorβ (TGF-β), bone morphogenetic proteins (BMP's) [Majumdar, M. K., *J. Cell. Physiol.*, 189(3), pp. 275-84 (2001)], cartilage-derived morphogenetic protein (CDMP) [Luyten, F. P., *Acta Orthop. Scand. Suppl.*, 266, pp. 51-4 (1995)], Indian hedgehog protein (IHH protein) [St-Jacques, B. et al., *Genes Dev.*, 13(16), pp. 2072-86 (1999)], sonic hedgehog protein (SHH protein) [Iwamoto, M. et al., *Crit. Rev. Oral Biol. Med.*, 10(4), pp. 477-86 (1999)] or SOX-9 [Kolettas, E. et al., *Rheumatology*, 40(10), pp. 1146-56 (2001)] maybe added to the implanted synovial tissue to induce homogeneous differentiation into chondrocytes. The transforming factor is preferably administered in a controlled-release delivery system. Continued proliferation and cartilage production fill in the defect site, thereby repairing the defect. As the new cartilage is formed and densifies, it replaces the biodegradable matrix and the thin covering membrane dissolves or is integrated into the repair tissue, leaving behind a repaired lesion. Maintenance factors known in the art (e.g., IGF I, IGF II and IGF-BP's) may also be used to stabilize the repair cell population within the defect.

Transforming factors useful in the compositions and methods of this invention to promote cartilage repair include any peptide, polypeptide, protein or any other compound or composition that induces differentiation of the synovial-derived repair cells into chondrocytes that produce cartilage-specific proteoglycans and type II collagen. Transforming factors may also induce cells to form bone or other cell types. The ability of a compound or composition to induce or stimulate production of cartilage-specific proteoglycans and type II collagen in cells can be determined using assays known in the art [e.g., Seyedin et al., 1985, supra; Seyedin et al., 1987, supra]. The transforming factors useful in the compositions and methods of this invention include, for example, TGF-B's, TGF-α's, FGF's (acidic or basic) and BMP's, including BMP-2. These transforming factors may be used singly or in combination. Dimers and multimers of these factors may also be used. In addition, TGF-β may be used in combination with EGF.

In particular, TGF-βI or TGF-βII or BMP-2 may be used as the transforming factor. Other TGF-β forms (e.g., TGF-β, TGF-βIV, TGF-βV, or any member of the TGF-β superfamily) or polypeptides having TGF-β activity (see Roberts, 1990, supra) may also be useful for this purpose, as well as other forms of this substance to be detected in the future, and other growth factors.

In a preferred embodiment, a TGF-β concentration is preferably greater than 200 ng/ml of matrix and, most preferably, is greater than or equal to 500 ng/ml of solution or matrix. Alternatively, BMP may be used as a transforming factor at a preferable concentration of 100-2000 ng per ml. It will be appreciated that the preferred concentration of TGF-β or BMP to induce differentiation of synovial cells may vary with the particular species or individual to be treated.

The transforming factors in the compositions of this invention are applied in the defect site within the matrix. Their presence is thus restricted to a very localized site. This is done to avoid their free injection or infusion into a joint space. Such free infusion may produce the adverse effect of stimulating the cells of the surrounding synovial membrane to produce joint effusion.

In a preferred embodiment of this invention, the tissue or matrix to be implanted contains an anti-angiogenic agent in addition to TGF-β or BMP as the transforming factor.

In another embodiment of the present invention, the defect site is treated with a proteoglycan-degrading enzyme and/or another adhesion-enhancing compound as described above. The synovial membrane tissue or cultured synovial cells are first added to a biodegradable matrix system. The matrix system containing the synovial membrane tissue or cells in an adequate concentration (e.g., from 10,000 to 300,000 cells per milliliter of tissue, solution or matrix) is then implanted into the defect site. As described above, a thin covering membrane, artificial or natural, may be sealed over the defect surface to prevent loss of tissue into the joint space; however, particularly with smaller defects, a covering membrane may not be necessary, as matrix containing synovial membrane tissue or cells used to fill the defect will tend to remain within the defect. Cells within synovial membrane tissue used to fill the defect will tend to proliferate within the matrix system.

In embodiments using the matrix system as discussed above, a transforming factor, preferably a member of the TGF-β superfamily, is provided within the matrix system upon implantation, such that the implanted synovial cells are induced to differentiate into cartilage-producing chondrocytes. A delivery system may be employed with the transforming factor to enable the implanted cells to have continued and prolonged exposure to the transforming factor. Examples of appropriate delivery systems include polylactate microspheres and liposomes. A delivery schedule may be developed based on the specific parameters of the case such as the size and density of the defect site, concentration of target cells at a given time and transforming factor used. Such systems are disclosed in U.S. Pat. No. 5,206,023.

Additionally, if the defect is large relative to the concentration of cells within the synovial membrane sample or cell suspension used to fill the defect, a proliferation agent may be added to the synovial membrane sample or matrix as a means of expanding the number of synovial cells filling the defect. The proliferation agent or agents should be present in an appropriate concentration range to have a proliferative effect on the synovial cells within the defect. Preferably, the same agent should also have a chemotactic effect on the cells (as in the case of TGF-β); however, a factor having exclusively a proliferative effect may be used, particularly when a covering membrane is present to retain tissue and cells in the defect space. Alternatively, to produce a chemotactic effect on the cells placed in the defect, followed by induction of cell proliferation, two different agents may be used, each one having just one of those specific effects (either chemotactic or proliferative). Such agents are described in U.S. Pat. No. 5,206, 023. Fibronectin or other cell adhesion promoting factors may also be included in the matrix, as described in U.S. Pat. No. 5,206,023. Subsequent administration of a transforming factor as discussed above will induce the cells in the synovial membrane sample or cell suspension to differentiate into cartilage-producing chondrocytes. A controlled-release delivery system as discussed above may be employed to administer either or both of the proliferation agent and transforming factor.

In another embodiment of the present invention, in particular where the cartilage defect is full-thickness, one or more anti-angiogenic agents may be added to the synovial tissue, cell solution or matrix in an appropriate concentration range to prevent blood vessel growth into the cartilage tissue. Anti-angiogenic agents that may be used include any agent with biological activity that prevents ingrowth of blood vessels from the underlying bone tissue or neighboring synovial membrane into the cartilage tissue. Such anti-angiogenic agents are described in U.S. Pat. No. 5,853,746. Some examples of anti-angiogenic agents that may be useful for this invention are set forth above. The anti-angiogenic agent should be freely available to provide immediate activity and may also be present in a sustained-release form, e.g., associated with a delivery system for prolonged activity. Such systems are also disclosed in U.S. Pat. No. 5,853,746.

Alternatively, a membrane is disposed toward the bone tissue before implantation of the synovial membrane tissue, cells or matrix, to prevent the ingrowth of blood vessels and perivascular cells from the underlying bone marrow spaces or other surrounding tissue, thereby preventing the formation of bone tissue in the defect site. See U.S. Pat. Nos. 5,270,300 and 5,853,746. Anti-inflammatory agents may also be added in a controlled-release delivery system to prevent contamination with inflammatory cells.

In the above embodiments involving either in vitro cell culture or in situ transformation of synovial tissue or cells, synovial cells may be stably or transiently transfected with one or more chondrogenic genes. In the case of in vitro cell culture, this will be done before implantation into the defect, during the in vitro cell culture process. In the case of in situ transformation, transfection may also be accomplished in situ, by means known in the art, such as liposomes or adenoviral vectors.

One embodiment involving transfected chondrogenic genes is the use of stacks of synovial membrane tissue interleaved with the selected transfection vehicle in the defect so as to effect transfection in situ. Examples of chondrogenic genes include, but are not limited to, BMP, BMP-2, BMP-9, TGF-β, CDMP, IHH, SHH and SOX-9, and may be transfected according to methods known in the art, such as electroporation, liposomal delivery and viral vectors, as appropriate to the circumstance. DNA encoding chondrogenic genes known in the art may be obtained through PCR amplification of commercially available DNA libraries using primer sequences obtained from published DNA sequence of the chondrogenic gene or genes to be transfected.

In each of the above embodiments, tissue or matrices may nonspecifically become mineralized or calcified in the repair tissue area. Calcification or mineralization inhibitors such as bisphosphonates may therefore be added to the tissue or matrix to prevent such unwanted mineralization or calcification and preserve the hyaline-like character of the repair tissue. It is also desirable to inhibit differentiation of chondrocytes into hypertrophic chondrocytes that act to mineralize the tissue repair area. This may be accomplished by the use of parathyroid hormone receptor protein or other known active agents.

In each of the foregoing embodiments, following implantation of the synovial membrane tissue or cells, and optionally covering the filled defect with the biodegradable covering membrane, the joint space is surgically closed in layers.

The methods of this invention allow for a treatment of cartilage defects in animals, including humans, that is simple to administer and is restricted in location to an affected joint area. The entire treatment may be carried out by arthroscopic, open surgical or percutaneous procedures.

In order that the invention described herein may be more fully understood, the following examples are set forth. It should be understood that these examples are for illustrative purposes and are not to be construed as limiting this invention in any manner.

EXAMPLE I

Use of Synovial Membranes to Cover Articular Cartilage Defects In Vivo

In order to test the effectiveness of using a synovial membrane to cover articular cartilage defects, defects 5 mm wide, 10 mm long and 0.7 mm deep were created with a planing instrument in mature goats. The new defects were filled with a fibrin matrix containing free proliferation agent (IGF-1) at a concentration of 40 ng/ml and a liposome-encapsulated transforming growth factor (BMP-2) at a concentration of 1.0 µg/ml. The defect was then covered with a synovial membrane that was excised from the joint wall, of the same dimensions, and sutured to the defect borders by vycril 7.0 suture material by using single interrupted sutures. After closure of the joint the animals were kept with the joint immobilized in a soft cast over 4 weeks (n=6 animals). Following euthanasia and histological analysis, it was found that the synovial membrane was well incorporated into the surrounding cartilage tissue border, and it had also transformed into cartilage-like tissue. In 3 of the animals, the synovial tissue was oriented with the synovial lining cells towards the joint cavity and in 3 of them the lining cells were oriented towards the defect space. In both groups similar results were obtained (i.e., covering membrane orientation does not appear to play a significant role in the methods of this invention).

EXAMPLE II. A

Use of Synovial Bits to Repair Articular Cartilage Defects In Vivo

In large articular cartilage defects, the process of synovial cell migration from the synovium into the articular cartilage defect to populate the defect with cells that can be transformed into chondrocytes to repair the cartilage may be too slow or provide insufficient numbers of cells to achieve complete filling by cell proliferation and tissue differentiation within the first few weeks following surgery. To provide a greater number of sources of cells for repair, synovial membrane material was cut into small tissue bits and mixed into a fibrin matrix and deposited, together with a transforming factor, within a defect. The defect was then covered by a synovial covering membrane, as described in the Example I above. All aspects of the experiment were as described above except for the addition of synovial bits to the fibrin matrix. Upon sacrifice of the animal, numerous areas of tissue transformation were present, and the number of repair cells was sufficient for the formation of new cartilage tissue.

EXAMPLE II. B

Partial Devitalization of Synovial Tissue Prior to Transplantation

The experiment in II. A. (above) was modified such that the transplanted synovial covering membrane was frozen a single time and immediately thawed. This was also done with the synovial tissue bits in order to reduce the number of macrophages present in the synovial tissue. By adding this step, a more homogenous transformation of cartilage tissue was achieved.

EXAMPLE III

Use of Stacks of Synovial Membranes to Repair Articular Cartilage Defects In Vivo The experiment described in Example I (above) was modified such that the defect was filled with stacks of synovial membranes of the approximate dimensions of the defect itself. Prior to placement in the defect, each of the synovial membranes was soaked in a BMP-2 solution at a concentration of 4.4 mg/ml, to induce transformation into cartilage tissue. Additionally, between the layers of synovial membranes, a small amount of fibrin matrix or microspheres containing transforming factors (BMP-2, 4.4 mg/ml) was deposited to allow for the controlled release of the transforming factor. Macroscopic results showed transformation of the synovial tissue into cartilage-like tissue.

EXAMPLE IV

Use of Cultured Synovial Cells to Repair Articular Cartilage Defects In Vivo Treatment of defects similar to those described in Example I (above) can be conducted such that following a surgical intervention in which an appropriate amount of synovial membrane and/or synovial fluid is extracted, preferably from the joint to be repaired, the synovial cells obtained are then cultured in vitro until a concentration of from 10,000 to 300,000 cells per milliliter of solution is reached. A proliferation agent can be used to expedite expansion of the cultured synovial cell population.

The cultured synovial cell population is then directly implanted into the defect site in suspension. Under local anesthesia, a small arthroscopic or surgical intervention is performed. The surface of the defect is dried by blotting the area using sterile absorbent tissue, and the defect volume is filled with a sterile proteoglycan degrading enzyme solution for a period of 2-10 minutes to degrade the proteoglycans present on the surface of the cartilage and, locally, to a depth of approximately 1 to 2 µm from the surface of the defect. The proteoglycan degrading enzyme is then removed and the defect is rinsed.

In suspension or a matrix (a preferred concentration being 10,000 to 300,000 cells per milliliter of solution or matrix), the cultured synovial cells are then implanted into the defect site, preferably in combination with a transforming factor, such as TGF-β, to promote differentiation of the synovial cells into cartilage-producing chondrocytes. In order to prevent loss of the implanted cells into the joint space, the surface of the defect site is covered with a thin biodegradable covering membrane, preferably a synovial membrane. The covering membrane is sealed to the edges of the defect site with sutures, fibrin glue, tissue transglutaminase, or the like. If sutures are used in conjunction with a synovial covering membrane, the sutures may be impregnated with a transforming factor such as BMP-2 at an appropriate concentration to promote differentiation of the synovial cells in the covering membrane into chondrocytes.

Following implantation of the cultured synovial cells and covering with the biodegradable covering membrane, the joint space is surgically closed in layers.

EXAMPLE V

Transformation of Synovial Tissue in Situ

The time course of synovial tissue transformation by BMP-2 in situ was examined in adult rabbits. The study consisted of five groups of five rabbits in each group. A collagenous matrix containing BMP-2-loaded liposomes at a concentration of 100 ng/ml was sutured to synovial membrane in the knee joint of each animal. Following implantation of the collagenous matrix, the joint space was surgically closed in layers.

Joint histology was examined at day 0, day 6, day 8, day 12 and day 14. Whole joints were fixed and embedded in plastic, after which 1.5 mm serial sections were made. In this way it was possible to observe changes in tissue composition over time. Four categories of tissue were identifiable: (1) normal synovial tissue; (2) new connective tissue; (3) new cartilage; and (4) new bone (with bone marrow).

On day 6, only normal synovial tissue and new connective tissue was observed. On day 8, cartilaginous foci appeared. On day 10, the new cartilage had acquired more mass. On day 12, bone foci appeared, and on day 14 a substantial amount of bone was seen in addition to the cartilage. These results indicate that synovial tissue in the knee joint contains adult stem cells that are capable of transformation into cartilage and bone under the proper conditions.

I claim:

1. A method for treating an articular cartilage defect in an animal, comprising:
    removing a portion of the synovial membrane from the animal; obtaining untransfected synovial cells from the removed synovial membrane; culturing and proliferating the untransfected synovial cells in vitro; and
    filling the cartilage defect with the cultured untransfected synovial cells, wherein an effective amount of a transforming factor is also used to fill the cartilage defect.

2. The method of claim 1, wherein an effective amount of an anti-angiogenic agent is also used to fill the cartilage defect to prevent ingrowth of vascular tissue and bone tissue formation.

3. A method for treating an articular cartilage defect in an animal, comprising:
    removing a portion of the synovial membrane from the animal;
    obtaining the individual synovial cells from the removed synovial membrane;
    culturing and proliferating the synovial cells in vitro;
    stimulating the synovial cells with a transforming factor to induce differentiation of the synovial cells into chondrocytes;
    stimulating the chondrocytes to produce a cartilage matrix in vitro; and
    filling the cartilage defect with the resultant cartilage tissue consisting of chondrocytes and their surrounding cartilage matrix.

4. The method of claim 3, further comprising the step of:
    subjecting the produced cartilage matrix to partial enzymatic digestion to release the cartilage matrix-forming chondrocytes before filling the cartilage defect.

5. The method according to any one of claims 1, 3 or 4, further comprising treating the defect site with an agent to degrade proteoglycans from the surface of the defect and removing the agent prior to the step of filling the defect.

6. The method of claim 5 wherein the agent to degrade proteoglycans is chondroitinase AC.

7. The method according to claim 2, wherein the anti-angiogenic agent is selected from the group consisting of suramin, angiostatin, metalloprotease inhibitors, anti-bFGF antibodies, anti-ESAF antibodies, fumagillin, and AGM-1470.

8. The method according to any one of claims 3 or 4, wherein the transforming factor is selected from the group consisting of TGF-β's, BMP's, CDMP, IHH, SHH and SOX-9.

9. The method of claim 3, further comprising the step of adapting in size and shape the cartilage produced in vitro to fit the defect site, prior to implanting the cartilage in the defect site.

10. A composition for the treatment of defects in cartilage comprising:
   a biodegradable matrix or matrix-forming material;
   a preparation of synovial cells that have not been transfected with a transforming factor gene; and
   an effective amount of a transforming factor to transform the synovial cells into chondrocytes.

11. The composition of claim 10, further comprising an effective amount of a proliferation agent to stimulate proliferation of synovial cells.

12. The composition of claim 10, further comprising an effective amount of an anti-angiogenic agent to prevent ingrowth of blood vessels into the cartilage.

13. The composition of claim 10, wherein the transforming factor is associated with a controlled-release delivery system.

14. The method according to any one of claims 1, 3, 4 or 9 further comprising covering the filled defect with a covering membrane to prevent loss of the cells filling the defect.

15. The method of claim 14 wherein the covering membrane is a synovial covering membrane.

16. The method according to any one of claims 1, 3 or 4, further comprising treating the defect site with a mineralization inhibitor.

17. The composition of claim 10 further comprising a mineralization inhibitor.

18. The method according to any one of claims 1, 3 or 4, further comprising treating the defect site with a calcification inhibitor.

19. The composition of claim 10, further comprising a calcification inhibitor.

20. The method according to any one of claims 3 or 4, further comprising treating the defect site with fibrin glue or transglutaminase and/or fibronectin, to enhance adhesion of the matrix to the defect site.

21. The composition of claim 10, further comprising fibrin glue or transglutaminase and/or fibronectin, to enhance adhesion of the matrix to the defect site.

22. The method according to any one of claims 3 or 4, wherein the transforming factor is associated with a controlled-release delivery system.

23. The method of claim 15 wherein sutures soaked in transforming factor are used to attach the covering membrane to the defect border.

24. The method of claim 1, wherein the animal is a human.

25. The method of claim 3, wherein the animal is a human.

* * * * *